(12) United States Patent
Borck

(10) Patent No.: US 8,852,622 B2
(45) Date of Patent: Oct. 7, 2014

(54) COATED IMPLANT COMPOSED OF A BIOCORRODIBLE MAGNESIUM ALLOY

(75) Inventor: Alexander Borck, Aurachtal (DE)

(73) Assignee: Biotronik AG, Buelach (CH)

( * ) Notice: Subject to any disclaimer, the term of this patent is extended or adjusted under 35 U.S.C. 154(b) by 452 days.

(21) Appl. No.: 13/224,578

(22) Filed: Sep. 2, 2011

(65) Prior Publication Data

US 2012/0078349 A1 Mar. 29, 2012

Related U.S. Application Data

(60) Provisional application No. 61/387,048, filed on Sep. 28, 2010.

(51) Int. Cl.
*A61F 2/00* (2006.01)
*A61L 31/16* (2006.01)
*A61L 31/14* (2006.01)
*A61L 27/54* (2006.01)
*A61L 27/34* (2006.01)
*A61L 27/04* (2006.01)
*A61L 31/10* (2006.01)
*A61L 31/02* (2006.01)

(52) U.S. Cl.
CPC .............. *A61L 31/022* (2013.01); *A61L 31/16* (2013.01); *A61L 2300/416* (2013.01); *A61L 31/148* (2013.01); *A61L 27/54* (2013.01); *A61L 27/34* (2013.01); *A61L 27/04* (2013.01); *A61L 31/10* (2013.01); *A61L 2420/08* (2013.01)
USPC ........................................................ 424/423

(58) Field of Classification Search
None
See application file for complete search history.

(56) References Cited

U.S. PATENT DOCUMENTS

2010/0211158 A1* 8/2010 Haverty et al. ............... 623/1.15
2011/0076319 A1* 3/2011 Orlowski et al. ............. 424/426

FOREIGN PATENT DOCUMENTS

WO WO 2006/108065 10/2006
WO WO 2008/092436 8/2008

OTHER PUBLICATIONS

European Search Report issued in corresponding European Application No. 11179132.3 on Feb. 28, 2012.

* cited by examiner

*Primary Examiner* — Paul Dickinson
(74) *Attorney, Agent, or Firm* — Greer, Burns & Crain, Ltd.

(57) ABSTRACT

One embodiment of the invention relates to a coated implant having a base body composed of a biocorrodible magnesium alloy. The coating of the implant comprises:

(i) a base layer, which is applied to the base body, composed of a basic polymer having a repeater unit that contains units of formula (1) or (2)

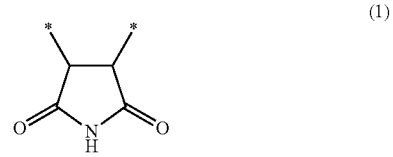

(1)

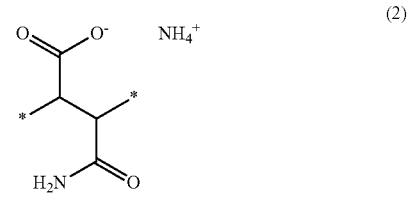

(2)

and (ii) a polymeric cover layer that is applied directly to the base layer.

20 Claims, 1 Drawing Sheet

COATED IMPLANT COMPOSED OF A BIOCORRODIBLE MAGNESIUM ALLOY

RELATED APPLICATION

This patent application claims the benefit of U.S. Provisional Patent Application No. 61/387,048, filed on Sep. 28, 2010, which is hereby incorporated by reference in its entirety.

TECHNICAL FIELD

One embodiment of the invention relates to a coated implant having a base body composed of a biocorrodible magnesium alloy.

BACKGROUND

Implants are utilized in modern medical technology in a variety of applications. They are used for example, to support vessels, hollow organs, and ductal systems (endovascular implants e.g. stents), to fasten and temporarily fix tissue implants and tissue transplants in position, as well as for orthopedic purposes such as pin, plate, or screw and other applications. The stent is a form of an implant that is used particularly frequently.

Stent implantation has become established as one of the most effective therapeutic measures for treating vascular disease. Stents are used to provide support in a patient's hollow organs. To this end, some stents have a filigree support structure composed of metallic struts; the support structure is initially present in a compressed form for insertion into the body, and is expanded at the application site. One of the main applications of stents of this type is to permanently or temporarily widen and hold open vasoconstrictions, in particular constrictions (stenoses) of the coronary arteries. In addition, aneurysm stents are known, for example, which are used primarily to seal the aneurysm. They also perform the support function.

Some stents include a circumferential wall having a support force that suffices to hold the constricted vessel open to the desired extent; stents also include a tubular base body through which blood continues to flow without restriction. The circumferential wall can be formed by a latticed support structure that enables the stent to be inserted, in a compressed state with a small outer diameter, until it reaches the constriction in the particular vessel to be treated, and to be expanded there, e.g. using a balloon catheter, to the extent at which the vessel has the desired, increased inner diameter. Alternatively, materials having a memory effect, such as Nitinol, are capable of self-expansion in the absence of a restoring force that holds the implant at a small diameter. The restoring force can be exerted on the material by a protective tube.

The implant, in particular the stent, has a base body composed of an implant material. An implant material is a non-living material that is used for a medical application and interacts with biological systems. A prerequisite for the use of a material as an implant material that comes in contact with the body environment when used as intended is its biocompatibility. "Biocompatibility" refers to the capability of a material to evoke an appropriate tissue response in a specific application. This includes an adaptation of the chemical, physical, biological, and morphological surface properties of an implant to the recipient tissue, with the objective of achieving a clinically desired interaction. The biocompatibility of the implant material is furthermore dependent on the time sequence of the response of the biosystem in which the implant is placed. For example, irritations and inflammations, which can cause tissue changes, occur over the relative short term. Biological systems therefore respond differently depending on the properties of the implant material. Depending on the response of the biosystem, implant materials can be subdivided into bioactive, bioinert, and degradable/resorbable materials.

Implant materials include polymers, metallic materials, and ceramic materials (as coating, for example). Biocompatible metals and metal alloys for permanent implants contain e.g. stainless steels (e.g. 316L), cobalt-based alloys (e.g. CoCrMo casting alloys, CoCrMo forging alloys, CoCrWNi forging alloys, and CoCrNiMo forging alloys), pure titanium and titanium alloys (e.g. CP titanium, TiAl6V4 or TiAl6Nb7), and gold alloys.

It is furthermore known that a greater level of biocompatibility can be achieved by coating implant materials with particularly tissue-compatible materials. These materials are usually organic or synthetic-polymeric in nature and are partially of natural origin. Further strategies for preventing restenosis focus on inhibiting proliferation using medication e.g. treatment using cytostatic agents. The active ingredients can be provided e.g. on the implant surface in the form of a coating.

The use of biocorrodible magnesium alloys for temporary implants having filigree structures is made difficult, in particular, by the fact that the implant degrades very rapidly in vivo. Various approaches to reducing the rate of corrosion, i.e. the degradation rate, are under discussion. For example, attempts are being made to slow the degradation of the implant material by developing alloys for this purpose.

SUMMARY

One or more of the aforementioned disadvantages of the prior art are eliminated or at least lessened by the implant, according to some embodiments of the invention, which includes a base body composed of a biocorrodible magnesium alloy and a coating. One example embodiment of a coating of an implant embodiment comprises:
(i) a base layer, which is applied to the base body, composed of a basic polymer having a repeater unit that contains units of formula (1) or (2)

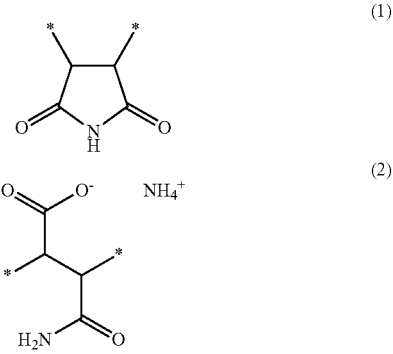

and
(ii) a polymeric cover layer that is applied directly to the base layer.

DESCRIPTION OF THE DRAWINGS

The invention is explained in greater detail below and the related figures. They show.

DETAILED DESCRIPTION

Figure 1:
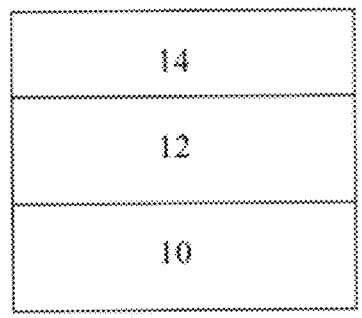
FIG. 1 a schematic depiction of the structure of the coating according to the invention.

At least some invention embodiments are based on the discovery that the corrosion of implants composed of biocorrodible magnesium alloys can be delayed by applying a double-layer, polymeric coating of a base layer, which is applied to the base body, and a cover layer which covers this base layer. In some embodiments, the polymer of the base layer includes an imide group having formula (1) or an amide ammonium salt having formula (2) as a basic component of its repeating unit. A basic micro-environment on the surface of the base body delays the degradation of the magnesium alloy. The basic micro-environment is created by the polymer of the base layer that includes the stated group in the repeating units. The chemical potential can be altered locally by a coating system composed of a Lewis base and a polymeric cover layer.

The basic polymer of the base layer in some example embodiments is a polymer having formula (3) or (4):

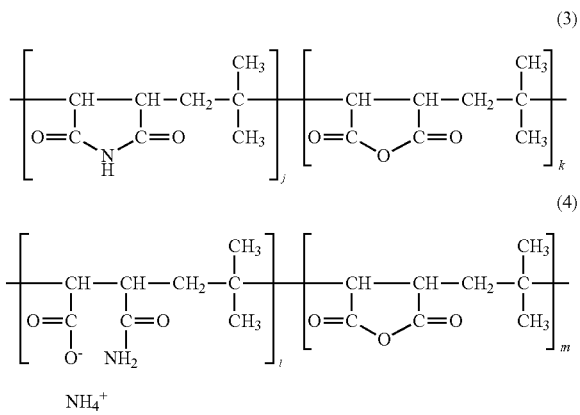

wherein j, k, l and m are selected such that the polymer has a molar mass in the range 50,000 to 100,000 g/mol, in particular 80,000 to 90,000 g/mol. These molar mass ranges have proven particularly advantageous in experimental testing. In some example embodiments, j=k and l=m. Polymers having formula (3) (polyisobutylene-alt-maleimide; CAS No: 89360-06-5) and formula (4) (CAS No: 52032-17-4) are commercially available.

According to a further embodiment, the cover layer includes poly(lactide-co-glycolide) (PLGA), or it is composed of this polymer. The cover layer can also contain an active ingredient.

According to the invention, a coating refers to the application, at least in sections and in some examples of the entirety, of the components of the coating on the base body of the implant. Preferably, the coating covers the entire surface of the base body of the implant. An example layer thickness is in the range of 1 nm to 100 μm, and another example 300 nm to 15 μm. Other thicknesses may also be used, with examples including less than 1 nm and greater than 100 μm. The coating according to the invention can be applied directly to the implant surface, or one or more further intermediate layers are provided; the base body of the implant may contain an organic base layer that improves the adhesion of the coating according to the invention. One or more further layers ("top coat" layers, for instance) can be applied to the coating according to the invention. Methods for coating implants are known to a person skilled in the art, and include by way of example and not limitation, spraying, dipping, rolling, and others.

Within the scope of the invention, those alloys are referred to as being biocorrodible that degrade/convert in a physiological environment, and therefore the part of the implant composed of the material is no longer present or at least substantially no longer present.

In this context, a magnesium alloy is understood to be a metallic microstructure having magnesium as the main component. The main component is the alloy component that comprises the largest weight component of the alloy. In some examples the main component is more than 50% by weight, and in some others more than 70% by weight. The composition of the alloy should be selected such that it is biocorrodible. Artificial plasma is used as a test medium to test the corrosion behavior of a potential alloy, the artificial plasma being specified according to EN ISO 10993-15:2000 for biocorrosion tests (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). To perform the test, a sample of the alloy to be investigated is stored in a closed sample container with a defined quantity of the test medium at 37° C. and pH 7.38. Samples are taken at certain time intervals, which are based on the anticipated corrosion behavior, of a few hours to several months, and they are examined in a known manner for traces of corrosion. The artificial plasma according to EN ISO 10993-15:2000 corresponds to a blood-like medium and therefore provides a way to reproducibly adjust a physiological environment within the scope of the invention.

In this context, the term "corrosion" refers to the reaction of a metallic material with its environment, inducing a measurable change to the material that causes the function of a component to become impaired if the material is used in the component. In this case, a corrosion system is composed of the corrosive metallic material and a liquid corrosion medium, the composition of which adjusts the conditions in the physiological environment, or is a physiological medium, blood in particular. In terms of the material, corrosion is influenced by various factors such as the composition and pretreatment of the alloy, microscopic and submicroscopic inhomogeneities, boundary zone properties, the temperature and voltage state, and, in particular, the composition of a layer that covers the surface. In terms of the medium, the corrosion process is influenced by conductivity, temperature, temperature gradients, acidity, salinity, the surface-to-volume ratio, concentration difference, and flow velocity.

Redox reactions take place at the phase interface between the material and the medium. To achieve a protective or inhibitive effect, existing protective layers and/or the products of the redox reactions can form a structure that is sufficiently impermeable to the corrosion medium, has an increased thermodynamic stability relative to the environment, and is poorly soluble or insoluble in the corrosion medium. Adsorption and desorption processes take place in the phase interface, specifically in a double layer that forms in this region. The processes in the double layer are characterized by the transport and diffusion processes that take place there. A gradual alkalization of the double layer is typically observed with magnesium alloys. Deposits of impurities, contaminants, and corrosion products influence the corrosion process. The processes that take place in corrosion, in particular the velocity-determining step, are thus highly complex and cannot be predicted, or only to a slight extent, particularly in conjunction with a physiological corrosion medium, i.e. blood or artificial plasma, since comparative data are unavailable. For this and other reasons, it is unknown and is beyond a person skilled in the art to find a corrosion-inhibiting coating, i.e. a coating that is used only to temporarily reduce the corrosion rate of a metallic material, which has the aforementioned composition, in a physiological environment. This applies in particular for stents that are exposed locally to high plastic deformations when implanted. Conventional designs that include rigid corrosion-inhibiting layers are unsuitable for use in conditions of that type.

The corrosion process can be quantified by stating a corrosion rate. Rapid degradation is associated with a high corrosion rate, and vice versa. An implant that has been coated according to some embodiments of the invention will have a reduced corrosion rate relative to the decomposition of the entire molded body. In some embodiments, the corrosion rate of coated implant will be no more than half that of the same implant without a coating (that is, the coated implant will take twice as long to corrode than will the uncoated implant). In other embodiments the corrosion rate will be faster or slower than this. The corrosion-inhibiting coating according to the invention can itself decompose over time, or can protect the regions of the implant it covers only to a continually decreasing extent. The graph of the corrosion rate for the entire implant is therefore non-linear for at least some embodiments. Instead, for at least some embodiments, the corrosion rate is relatively low at the beginning of the corrosive processes that set in, and it increases over time. This behavior is understood, within the scope of the invention, as a temporary reduction in the corrosion rate and characterizes the corrosion-inhibiting coating. In the case of coronary stents, the mechanical integrity of the structure should be maintained over a period of three to six months after implantation.

An important benefit of at least some invention embodiments includes that because of the reduced corrosion rate achieved, it is possible to utilize implants having thinner metallic wall thicknesses and accordingly of a smaller profile and lower weight as compared to implants of the prior art that did not include a coating of the invention. With a tubular stent being one example, coatings of the invention can lead to a smaller diameter stent which will achieve important benefits of increased ease of travel through hollow organs, reduced frictional contact and impact with organ walls (leading to lowered levels of irritation/inflammation), applications in smaller diameter organs that are not accessible to larger diameter stents, and other important benefits.

Implants, within the scope of the invention, are devices that are inserted into the body using a surgical procedure, and comprise fastening elements for bone, such as screws, plates, or nails, surgical suture material, intestinal clamps, vessel clips, prostheses in the region of hard and soft tissue, and anchor elements for electrodes, in particular pacemakers or defibrillators. The implant is composed entirely or in parts of the biocorrodible material. If only parts of the implant are composed of the biocorrodible material, then these parts are coated accordingly in some invention embodiments. The implant is preferably a stent.

The cover layer can contain one or more active ingredients that are released after implantation. The active ingredient can be embedded in the polymeric material or otherwise included.

According to the invention, an active ingredient is a medicinal agent having a pharmaceutical effect, and which is used in the human body or animal body to cure, alleviate, prevent, or detect illness. Active ingredients include paclitaxel, sirolimus, and their derivatives, as well as other materials. In particular, active ingredients are advantageous that act on mTOR, and RAS inhibitors, in particular those that prevent the adhesion of RAS to the cell membrane.

Turning now to the drawings, FIG. 1 shows a highly schematicized illustration of the structure of a coating according to an invention embodiment. A base body 10 composed of a biocorrodible magnesium alloy is covered by a polymeric base layer 12. A polymeric cover layer 14 is applied directly to base layer 12.

The invention is explained in greater detail below with reference to an example embodiment.

EMBODIMENT

A stent composed of a biocorrodible magnesium alloy is immersed in a solution of polyisobutylene-alt-maleimide (2 g in 40 ml DMF) for 45 minutes at room temperature. The stent is removed, dabbed dry, and then allowed to air-dry for 30 minutes on a lint-free towel. The stent is then immersed in a solution of 0.2 g poly(lactide-co-glycolide) ("PLGA") (RESOMER® RG 502, available from Evonik Rohm GmbH); in 40 ml chloroform ($CHCl_3$) for 40 seconds at room temperature. The stent is then dabbed once more and dried for 1 hour at 75° C. in an oven.

Stents were tested as follows:

Coated and uncoated stents composed of a biocorrodible magnesium alloy were mounted on a balloon catheter. For the corrosion experiment, the stents were immersed, with the balloon, in 200 ml of a PBS solution (100 mM; pH 7.38), and dilated and released in this solution for a sufficient period of time. The solution was stirred and kept at room temperature.

Figure 2:
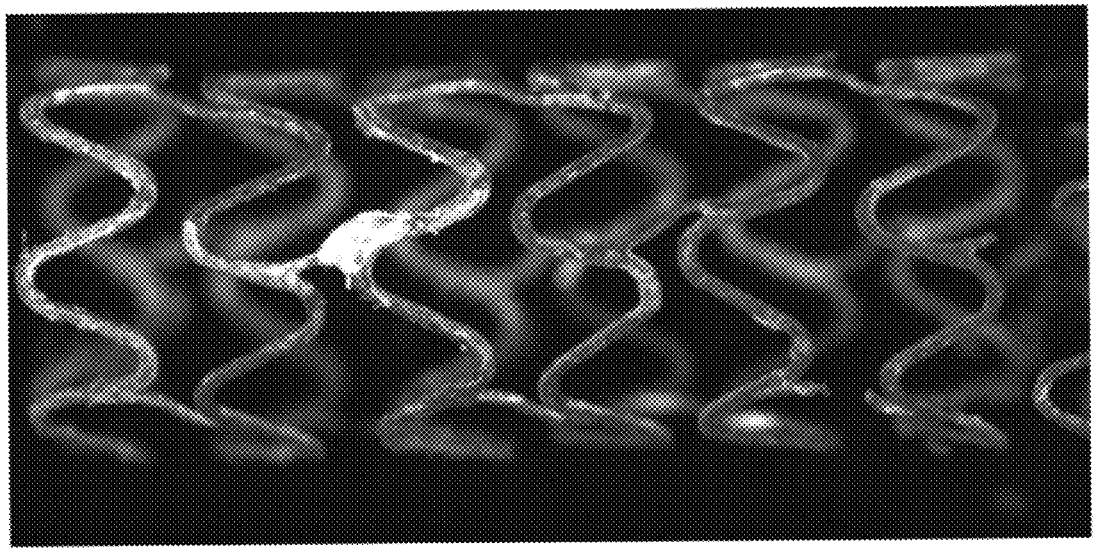
FIG. 2 a light-microscopic photograph of a coated stent after testing.

FIG. 2 shows a light-microscopic photograph of a stent, which was coated according to the invention, after testing. The structure of the stent is still intact, as is clearly shown. The metallic sheen is still clearly visible, thereby indicating that the base body has been attacked, but is still present.

For comparison purposes, stents without coating, stents that comprise only a base layer, only a cover layer, and a homogeneous mixture of the polymeric materials of the base layer and cover layer were subjected to the same corrosion test for the same period of time. All of these stents dissolved completely under the same conditions; in fact, not even fragments thereof could be found for analysis. Polyisobutylene-alt-maleimide and PLGA alone thus did not inhibit corrosion.

A basic micro-environment is created by the polymer of the base layer that has an imide group in every second repeating unit. From a similar perspective, the electron density in the base layer is shifted toward the substrate, thereby making the substrate more "noble" and slowing its corrosion rate. This effect is observed when the base layer contains electron-pair donors, in particular elements of the 5th and/or 6th main group of the periodic table. The elements of these main groups, in particular the elements sulphur, nitrogen, phosphorous, and oxygen, have unpaired electron pairs that are easily displaced. These results confirm that chemical potential can be influenced locally by the basic micro-environment. The maleinimide group acts as an electron donor (Lewis base). The experiments show that the basic influence should be protected by a further polymer layer. This is an unexpected result.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implant having a base body composed of a biocorrodible magnesium alloy and a coating comprising:
(i) a base layer, which is applied to at least a portion of the base body, comprising a basic polymer having a repeater unit that contains units of one or more of formula (1) and (2)

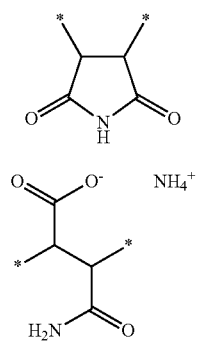

and
(ii) a polymeric cover layer that is applied directly to the base layer.

2. The implant according to claim 1, in which the basic polymer of the base layer is a polymer having a formula selected from (3) and (4)

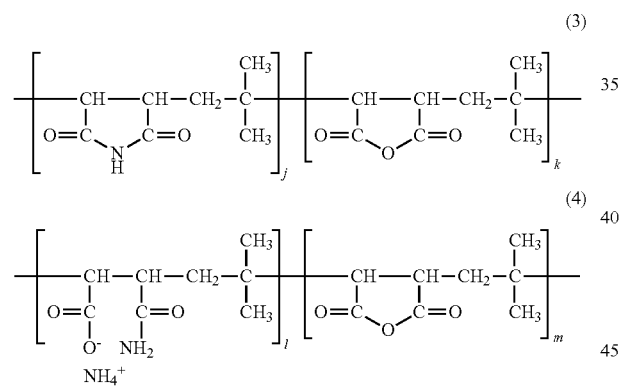

wherein j, k, l and m are selected such that the polymer has a molar mass in the range 50,000 to 100,000 g/mol.

3. The implant according to claim 1, in which the cover layer contains poly(lactide-co-glycolide) (PLGA).

4. The implant according to claim 1, in which the cover layer contains an active ingredient.

5. The implant according to claim 4, in which the active ingredient is one or more of paclitaxel, sirolimus, and a derivative of sirolimus.

6. The implant according to claim 1, wherein the implant is a stent.

7. The implant according to claim 1, wherein the base layer contains an electron-pair donor.

8. The implant according to claim 7, wherein the base layer, as the electron-pair donor, contains one or more elements of the $5^{th}$ main group of the periodic table.

9. The implant according to claim 7, wherein the base layer, as the electron-pair donor, contains one or more elements of the $6^{th}$ main group of the periodic table.

10. The implant according to claim 8 wherein the one or more elements of the $5^{th}$ main group are one or more of nitrogen and phosphorous.

11. The implant according to claim 9 wherein the one or more elements of the $6^{th}$ main group are one or more of sulfur and oxygen.

12. The implant according to claim 1 wherein the base layer has an imide group in every second repeating unit.

13. The implant according to claim 1 wherein the base layer has a thickness of between about 1 nm to 100 µm.

14. The implant according to claim 1 wherein the base layer has a thickness of between about 300 nm to 15 µm.

15. The implant according to claim 1 wherein and further comprising an organic layer between the base layer and the implant, the organic layer configured to improve the adhesion of the base layer to the implant.

16. The implant according to claim 1 wherein the base layer polymer has a molar mass between about 80,000 to 90,000 g/mol.

17. The implant according to claim 2 wherein j=k and l=m.

18. The implant according to claim 1, wherein the implant after coating with the base layer and the cover layer has a non-linear corrosion rate that increases over time when in a physiological environment.

19. A biocompatible stent for supporting a hollow organ in a mammal, the stent comprising:
a base body composed of a biocorrodible magnesium alloy including about 50% or more magnesium;
a coating covering the base body comprising:
(a) a base layer applied to the base body, the base layer comprising an electron pair donor and comprising a polymer having a formula selected from the group consisting of (1) and (2)

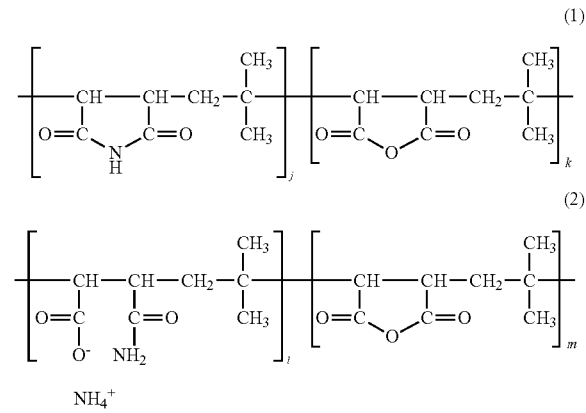

where j=k and l=m, the base layer having a molecular weight of between about 80,000 to 90,000 g/mol, and a thickness of between about 300 nm to 15 µm;
(b) a polymeric cover layer that is applied directly to the base layer and containing poly(lactide-co-glycolide) (PLGA); and,
wherein the coating provides the stent with a non-linear corrosion rate that increases over time when in a physiological environment.

20. The implant according to claim 19 wherein and further comprising an organic layer between the base layer and the base body, the organic layer configured to improve the adhesion of the base layer to the base body.

* * * * *